United States Patent [19]

Shearer et al.

[11] Patent Number: 6,126,521

[45] Date of Patent: Oct. 3, 2000

[54] PROCESS AND APPARATUS FOR MANUFACTURING ENDODONTIC INSTRUMENTS

[75] Inventors: Jack L. Shearer; Dane L. Shearer, both of York; Scott A. Munchel, Spring Grove; Lonnie M. Graybill, York, all of Pa.

[73] Assignee: Moyco Technologies, Inc., Montgomeryville, Pa.

[21] Appl. No.: 09/237,182

[22] Filed: Jan. 25, 1999

[51] Int. Cl.⁷ .................................................. B24B 1/00
[52] U.S. Cl. ........................................... 451/48; 451/222
[58] Field of Search ............................. 451/28, 48, 49, 451/54, 55, 57, 58, 65, 220, 222, 547; 72/338, 340, 341; 433/165, 224, 225

[56] References Cited

U.S. PATENT DOCUMENTS

| | | | |
|---|---|---|---|
| 4,611,508 | 9/1986 | Roane | 76/24 R |
| 4,999,952 | 3/1991 | Speiser et al. | 51/94 CS |
| 5,065,549 | 11/1991 | Speiser et al. | 51/288 |
| 5,417,525 | 5/1995 | Lenhart | 451/54 |
| 5,464,362 | 11/1995 | Heath et al. | 451/48 |
| 5,484,327 | 1/1996 | Kovach | 451/58 |
| 5,527,205 | 6/1996 | Heath et al. | 451/48 |
| 5,624,259 | 4/1997 | Heath et al. | 433/72 |
| 5,628,674 | 5/1997 | Heath et al. | 451/48 |
| 5,653,590 | 8/1997 | Heath et al. | 433/102 |
| 5,655,950 | 8/1997 | Heath et al. | 451/48 |
| 5,807,106 | 9/1998 | Heath | 433/102 |

*Primary Examiner*—Rodney A Butler
*Attorney, Agent, or Firm*—C. Clark Dougherty, Jr.

[57] ABSTRACT

An improved process for producing an endodontic instrument with a predetermined taper having a plurality of flutes, each with a predetermined number of spirals over a predetermined length of the instrument are provided. The process basically comprises providing a grinding wheel rotated about a first axis having a plurality of flute grinding ribs and a rolled deformed metal grinding rib extending from a periphery thereof. A rotating wire stock is fed past the plurality of flute grinding ribs and the rolled deformed metal grinding rib at a controlled rate along a second axis so that a separate flute is ground on the wire stock by each of the flute grinding ribs and rolled deformed metal is removed from the ground wire stock by the rolled deformed metal grinding rib. Simultaneously with feeding the rotating wire stock, the grinding wheel or the wire stock is translated such that a distance between the first and second axes increases as the bar stock is fed whereby the wire stock is tapered as the flutes are ground thereon.

29 Claims, 3 Drawing Sheets

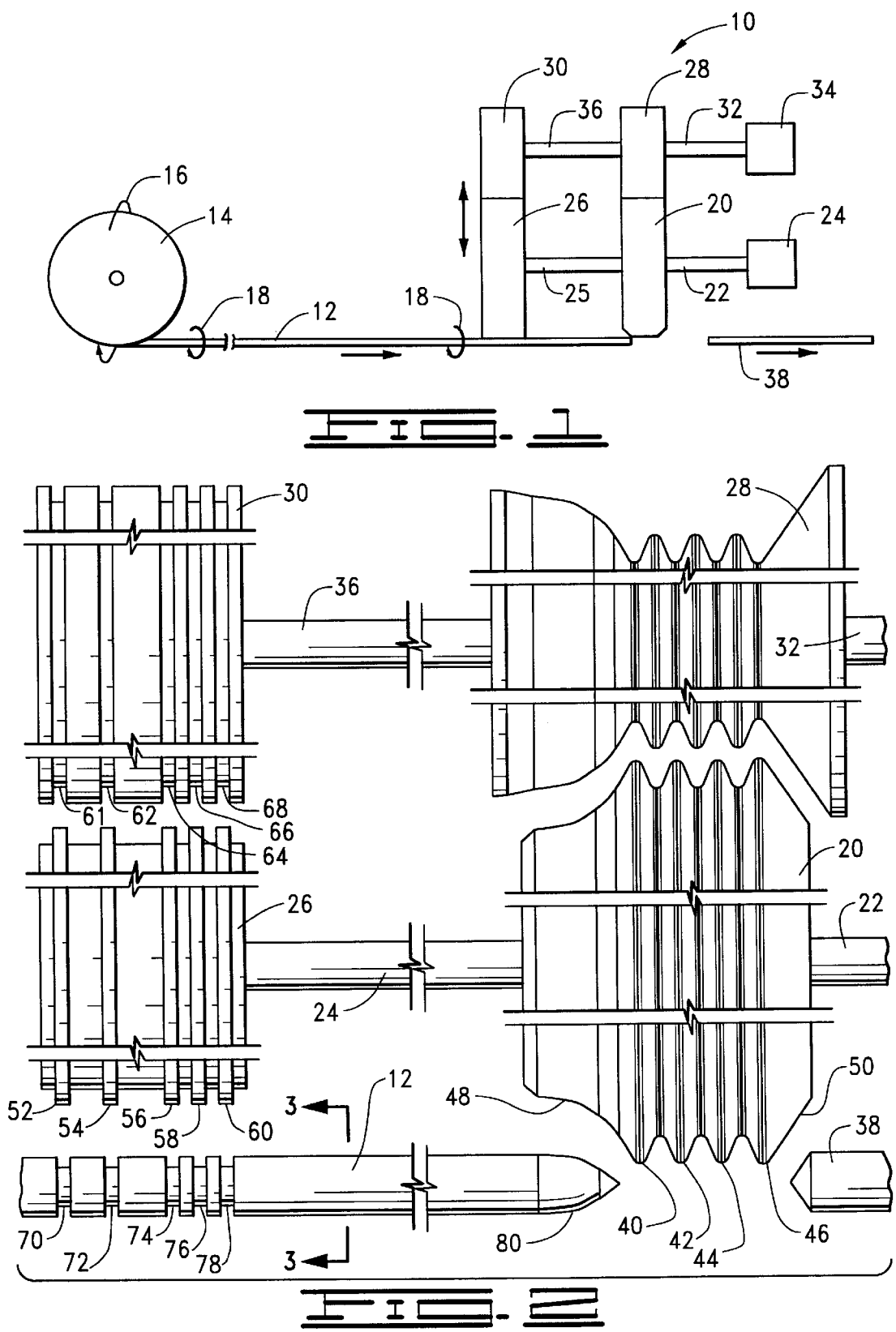

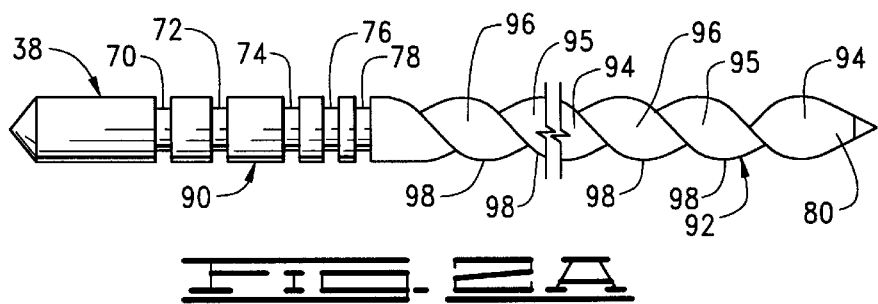
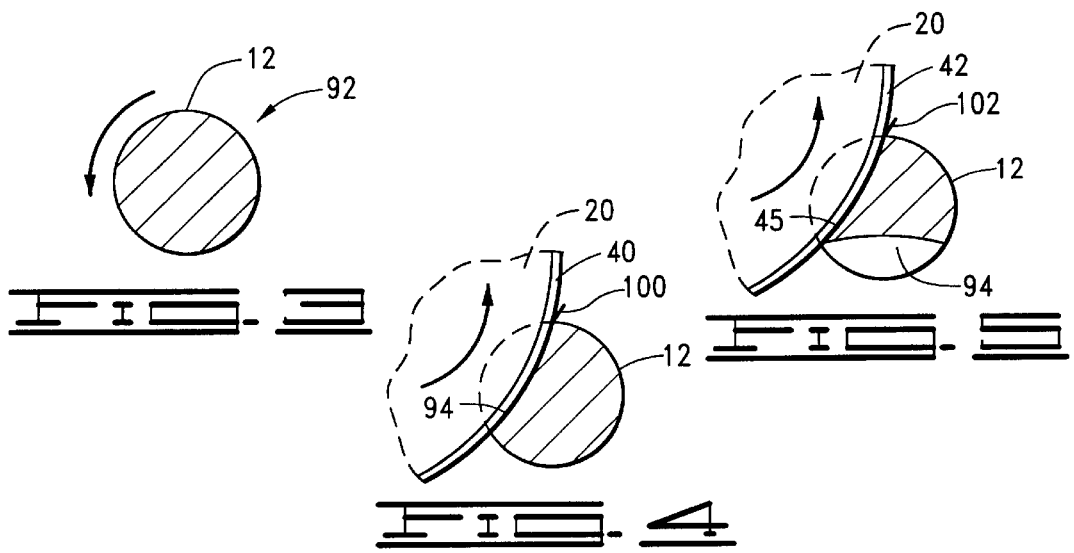
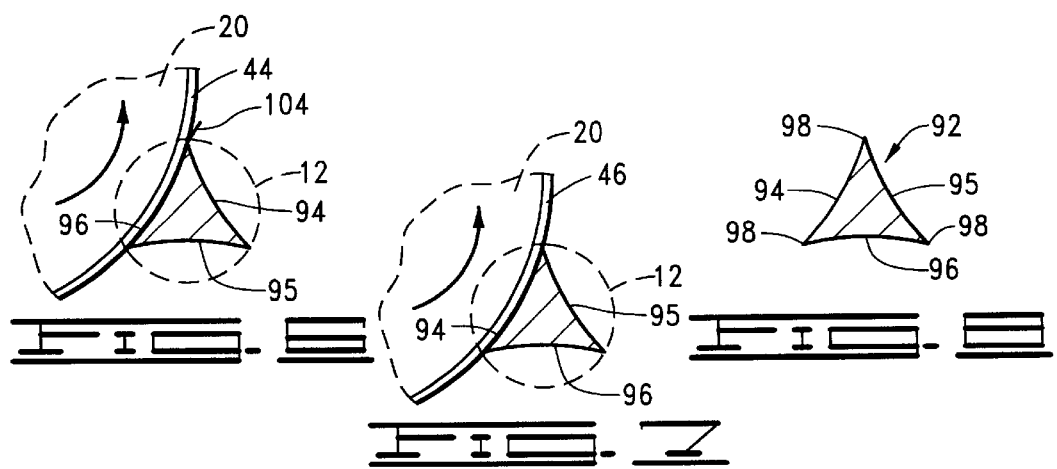

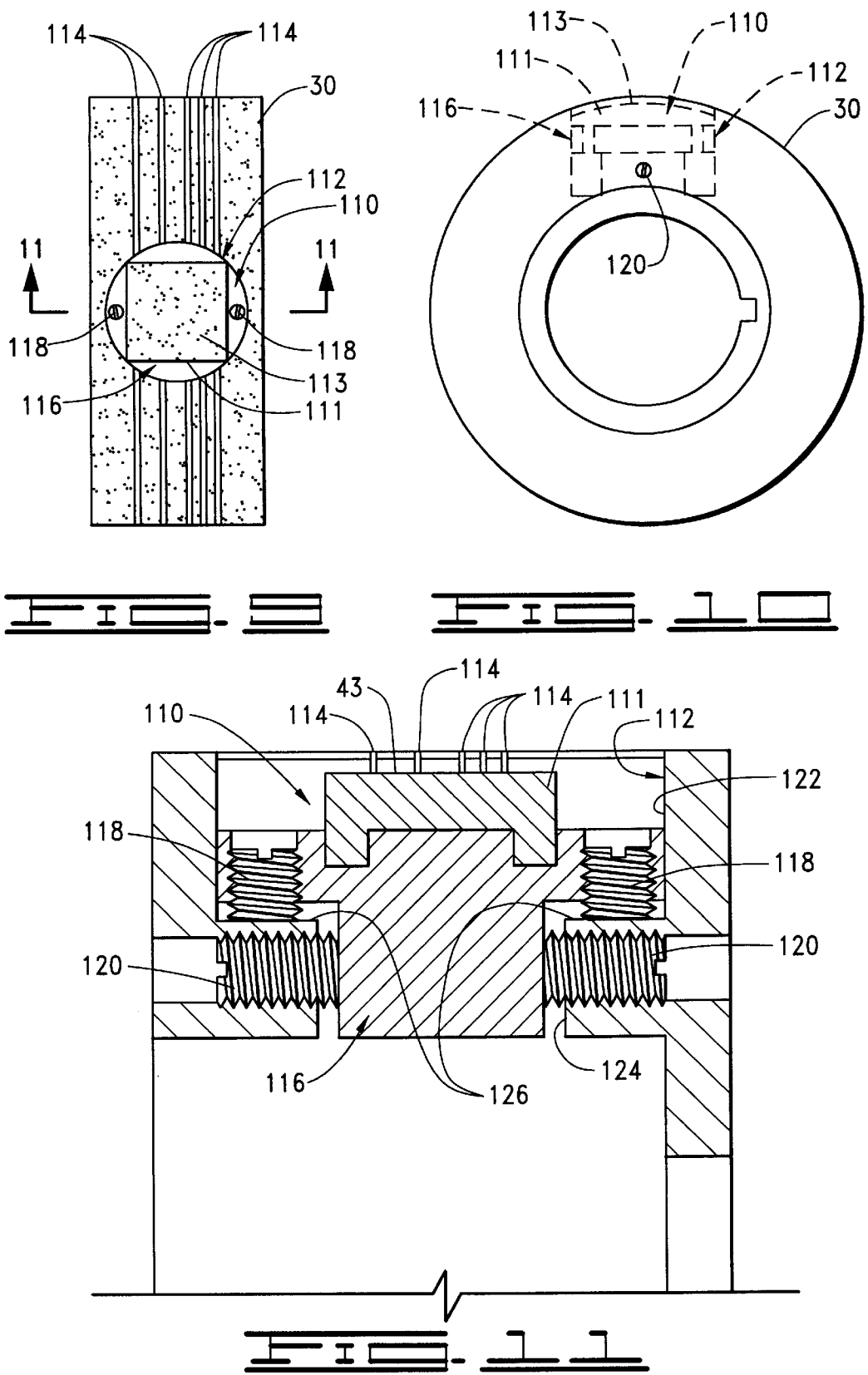

PROCESS AND APPARATUS FOR MANUFACTURING ENDODONTIC INSTRUMENTS

BACKGROUND OF THE INVENTION

1. Field of the Invention

The present invention relates to the manufacture of endodontic instruments, and more particularly, to the manufacture of such instruments by grinding a wire stock.

2. Description of the Prior Art

Endodontic instruments commonly referred to as files are utilized by dentists for cleaning and enlarging the root canals of human teeth. The purpose of the cleaning and enlarging procedure is to remove infected tissue from the root canals and enlarging the root canals so that they can be filled. A commonly used such endodontic instrument is known as a K-type file which has a tapered shaft including three or four spiral flutes along the length thereof. A preferred form of K-file includes three flutes, the cross-sectional shape of the shaft is triangular and the flutes form three spiral cutting edges along the length of the tapered portion of the shaft. Another type of endodontic instrument, known as a reamer, has three or four spiral flutes forming three or four spiral cutting edges thereon. These and other endodontic instruments are manufactured in accordance with standards set up by the American Dental Association and other standardizing bodies. For example, a standard K-type file ranges in tip size from 6 mm to 140 mm and in length from 21 mm to 31 mm. The total number of spirals varies depending on the size of the instrument and whether the instrument is a K-type file, a reamer or other type of file. The overall length of the spiraled portion of each instrument is a minimum of 16 millimeters and the diametric taper is 0.02 millimeter change in diameter per millimeter in length.

While various machining processes and apparatus for producing endodontic instruments have been developed and utilized, a particularly suitable process and apparatus are described in U.S. Pat. No. 4,999,952 dated Mar. 19, 1991 and U.S. Pat. No. 5,065,549 dated Nov. 19, 1991, both to Speiser et al., and both of which are incorporated herein and made a part hereof by reference thereto.

While the machining process and apparatus disclosed in the above mentioned patents to Speiser et al. have been used successfully for the manufacture of endodontic instruments of the types described above, there is a continuing need for improvements to such process and apparatus whereby the time and cost involved in machining each instrument are reduced.

SUMMARY OF THE INVENTION

The present invention provides an improved machining process and apparatus for manufacturing endodontic instruments which meet the needs described above and overcome the deficiencies of the prior art. The improved process of this invention for producing an endodontic instrument with a predetermined taper having a plurality of flutes, each with a predetermined number of spirals over a predetermined length of the instrument, basically comprises the following steps. A first grinding wheel rotated about a first axis is provided having a plurality of flute grinding ribs and a rolled deformed metal grinding rib extending from a periphery thereof. A rotating wire stock is fed past the plurality of flute grinding ribs and the rolled deformed metal grinding rib at a controlled rate along a second axis so that a separate flute is ground on the wire stock by each of the flute grinding ribs and rolled deformed metal is removed from the wire stock by the rolled deformed metal grinding rib. Simultaneously with the grinding of the flutes, the grinding wheel or the wire stock is translated, i.e., moved, such that a distance between the first and second axes increases as the wire stock is fed whereby a single pass of the wire stock past the flute grinding ribs and the rolled deformed metal grinding rib produces a tapered multi-fluted endodontic instrument which is substantially free of rolled deformed metal.

A preferred process of this invention includes the above steps in combination with the following additional steps. First and second tapered grinding surfaces are provided on the grinding wheel for forming a desired tip form such as a tapered tip on the rotating wire stock and for parting a previously formed multi-fluted tapered endodontic instrument from the rotating wire stock. In addition, a second grinding wheel having a plurality of depth indicating calibration grinding ribs extending from a periphery thereof which is rotated about a third axis is provided. The first grinding wheel is retracted from a flute grinding position with the rotating wire stock to a non-grinding position, and the rotating wire stock is fed forward a predetermined distance. Thereafter, the feed of the rotating wire stock is temporarily terminated while the first and second grinding wheels are advanced into grinding contact with the wire stock whereby a previously formed tapered multi-fluted endodontic instrument is parted from the wire stock, a tip having a desired form is ground on the wire stock and depth indicating calibration grooves are ground on the wire stock. The first and second grinding wheels are retracted whereby the first grinding wheel is returned to the flute grinding position and the second grinding wheel is returned to a position out of contact with the wire stock. The feed of the rotating wire stock is then resumed so that the proper taper and flutes are ground on the wire stock whereupon the above steps are repeated.

The grinding apparatus of this invention is basically comprised of a grinding wheel rotated about a first axis having a plurality of flute grinding ribs and a rolled deformed metal grinding rib extending from a periphery thereof; means for feeding a rotating wire stock past the plurality of flute grinding ribs and the rolled deformed metal grinding rib at a controlled rate and on an axis so that a separate spiraled flute is ground on the wire stock by each of the flute grinding ribs and rolled deformed metal extending from the last ground flute is removed therefrom by the rolled deformed metal grinding rib; and means for translating the first grinding wheel or the wire stock such that a distance between the first and second axes increases as the wire stock is fed and a tapered multi-fluted endodontic instrument is provided.

It is, therefore, a general object of the present invention to provide an improved process and apparatus for producing endodontic instruments.

Other and further objects, features and advantages of the present invention will be readily apparent to those skilled in the art upon a reading of the description of preferred embodiments which follows when taken in conjunction with the accompanying drawings.

BRIEF DESCRIPTION OF THE DRAWINGS

FIG. 1 is a schematic illustration of the improved grinding apparatus of this invention.

FIG. 2 is a partial enlarged view of the first and second grinding wheels, first and second dressing wheels and the ground wire stock of FIG. 1.

FIG. 2A is a side view of a tapered multi-fluted endodontic instrument produced by the grinding apparatus of this invention.

FIG. 3 is a cross-sectional view taken along line 3—3 of FIG. 2.

FIG. 4 is a cross-sectional view illustrating the wire stock and a portion of the first grinding wheel as a first flute is being ground thereon.

FIG. 5 is a cross-sectional view similar to FIG. 4 but showing the rotating wire stock as a second flute is being ground thereon.

FIG. 6 is a view similar to FIG. 5, but showing the rotating wire stock as a third and final flute is being ground thereon.

FIG. 7 is a view similar to FIG. 6, but showing the rotating wire stock as rolled deformed metal is being removed therefrom.

FIG. 8 is a cross-sectional view of the rotating wire stock after the three flutes have been ground thereon and rolled deformed metal has been removed therefrom.

FIG. 9 is a top more detailed view of the second dressing wheel illustrated schematically in FIG. 2.

FIG. 10 is a side view of the dressing wheel of FIG. 9.

FIG. 11 is a cross-sectional view taken along line 11—11 of FIG. 9.

DESCRIPTION OF PREFERRED EMBODIMENTS

The improved process and apparatus of the present invention basically comprises the steps and apparatus for carrying out the steps of providing a first grinding wheel rotated about a first axis having a plurality of flute grinding ribs and a rolled deformed metal grinding rib extending from a periphery thereof; feeding a rotating wire stock past the plurality of flute grinding ribs and the rolled deformed metal grinding rib at a controlled rate along a second axis so that a separate flute is ground on the wire stock by each of the flute grinding ribs and rolled deformed metal is removed from the wire stock by the rolled deformed metal grinding rib; and simultaneously translating the first grinding wheel on the wire stock such that a distance between the first and second axes increases as the wire stock is fed whereby a single pass of the wire stock past the flute grinding ribs and the rolled deformed metal grinding rib produces a tapered multi-fluted endodontic instrument which is substantially free of rolled deformed metal.

Other improved aspects of the process and apparatus of this invention include simultaneously grinding a tip of desired form on the rotating wire stock, grinding a plurality of depth indicating calibration grooves on the rotating wire stock and parting a previously formed tapered multi-fluted endodontic instrument from the rotating wire stock, all during the single pass of the rotating wire stock mentioned above.

Another improved aspect of the process and apparatus involves selectively accelerating the feed rate of the rotating wire stock past the plurality of flute grinding ribs and the rolled deformed metal grinding rib whereby the flutes are ground on the small diameter end portions of very small endodontic instruments being produced at a relatively slow rate and at an accelerated feed rate during the grinding of the flutes on the larger diameter portions of the instruments. This improvement reduces the overall instrument producing cycle time for small size endodontic instruments by as much as 40%.

Yet another improved aspect of the process and apparatus of this invention involves the use of a coil fed rotating wire stock system. Instead of utilizing bar length wire stock which requires reloading after every bar, a continuous feed reel of coiled wire stock is utilized which reduces reloading time and increases instrument production. The reel of coiled wire stock pays off wire as it is needed and also rotates on the same axis and at the same rate as the endodontic instrument being ground.

Still another improved aspect of the apparatus of this invention involves the use of an adjustable dressing wheel for dressing the depth indicating calibration forming grinding wheel mentioned above.

Referring now to the drawings, and particularly to FIG. 1, the apparatus of this invention for producing an endodontic instrument having a predetermined taper, having a predetermined number of flutes with a predetermined number of spirals, having a tapered tip and having a predetermined number of depth calibration grooves, all in a single cycle is illustrated. As shown in FIG. 1, a feed wire stock 12 is payed off of a rotatable reel 14 having a continuous coil of wire stock 12 wound thereon. As shown by the arrows 16 and 18, the reel 14 and wire stock 12 are rotated on the same axis and at the same rate as the portion of the wire stock 12 being ground. The rotation of the reel 14 and wire stock 12 is synchronized through a clutch mechanism, and the wire stock is fed using a lead screw mechanism or the like. The rotating feed stock 12 is fed in a direction towards and in contact with a first rotating grinding wheel 20. The grinding wheel 20 is generally disk-shaped and is disposed in a manner whereby its axis of rotation is parallel to the axis of rotation of the feed wire stock 12. A drive shaft 22 connects the first grinding wheel 20 to means for rotating the grinding wheel such as an electric motor 24, and a drive shaft 25 positioned coaxially with the drive shaft 22 connects the first rotating grinding wheel 20 to a second rotating grinding wheel 26. As will be described in detail hereinbelow, the first grinding wheel 20 includes a plurality of flute grinding ribs and a rolled deformed metal grinding rib for forming flutes on the endodontic instrument being produced and removing rolled deformed metal therefrom. The second grinding wheel 26 includes a plurality of depth indicating calibration groove grinding ribs formed thereon. A dressing wheel 28 is provided for dressing the surface of the first grinding wheel 20 and a second dressing wheel 30 is provided for dressing the surface of the second grinding wheel 26. The first dressing wheel 28 is rotated by a shaft 32 connected to a second rotator, e.g., electric motor 34, and a shaft 36 positioned coaxially with the shaft 32 is connected between the dressing wheels 28 and 30. The axes of the dressing wheel shafts 32 and 36 are positioned parallel to the axes of the grinding wheel shafts 22 and 24. The axis of the rotating wire stock 12 is also positioned parallel to the axes of the shafts 22 and 24. As will be described in detail hereinbelow, after a tapered multi-fluted endodontic instrument 38 is formed on an end portion of the rotating wire stock 12 which has been fed past the first grinding wheel 20. The instrument 38 is simultaneously parted from the rotating wire stock 12 while the tapered tip of the next instrument is ground on the rotating wire stock 12.

Referring now to FIGS. 2 and 2A, the grinding wheel-dressing wheel assembly and the rotating wire stock being ground are illustrated in FIG. 2 and the endodontic instrument produced which includes a tapered tip, spiraled flutes and depth calibration grooves is illustrated in FIG. 2A. As shown in FIG. 2, the first grinding wheel 20 includes on the periphery thereof three flute grinding ribs 40, 42 and 44 and a rolled deformed metal grinding rib 46. As is well understood by those skilled in the art, the grinding wheel 20 with three flute grinding ribs is for manufacturing three fluted endodontic instruments. Less or more flute grinding ribs can be included on the grinding wheel 20 for producing endodontic instruments having less or more than three spiraled flutes. As mentioned above and as will be further described below, the rolled deformed metal grinding flute 46 follows the spiraled path of the first flute grinding rib, i.e., rib 40, whereby rolled deformed metal extending from the last ground flute is removed therefrom. In addition, the first grinding wheel 20 includes a tip forming grinding contour 48 and a tapered instrument parting contour 50.

The second grinding wheel 26 includes a plurality of spaced depth calibration groove grinding ribs 52, 54, 56, 58 and 60 formed thereon. The depth calibration grooves on an endodontic instrument serve to provide an indication to the endodontist of the depth to which the tip of the instrument reaches within a root canal being cleaned. Depending on a particular size of the endodontic instruments being produced, more or less depth calibration groove grinding ribs can be included on the second grinding wheel 26, appropriately spaced from each other to provide the required number and spacing of depth calibration grooves on the instrument being manufactured.

The first grinding wheel 20 is rotated by the shaft 22 connected thereto and the shaft 25 connects the first grinding wheel 20 to the second grinding wheel 26 so that the grinding wheels 20 and 26 are rotated at the same rate. In addition, the first and second grinding wheels 20 and 26 are selectively movable towards and away from the rotating wire stock 12 by conventional apparatus (not shown). The dressing wheels 28 and 30 which are rotated simultaneously by means of the shafts 32 and 36 connected thereto are illustrated a distance apart from the first and second grinding wheels 20 and 26 for clarity. However, in operation, the surfaces of the dressing wheels 28 and 30 are periodically or continuously in contact with the peripheries of the grinding wheels 20 and 26, respectively, so as to maintain the shapes of the flute grinding ribs, the rolled deformed metal grinding rib and the depth calibration groove grinding ribs described above. As will be understood, if the first grinding wheel 20 includes more or less than three flute grinding ribs, the dressing wheel 28 includes the same number and shape of complimentary grooves therein.

The second dressing wheel 30 includes five complimentary grooves 61, 62, 64, 66 and 68 formed thereon for maintaining the size and shape of the groove grinding ribs 52–60 on the second grinding wheel 26. The first and second dressing wheels 28 and 30 are rotated simultaneously by the rotating shafts 32 and 36 connected thereto, and like the grinding wheels 20 and 26, the dressing wheels 28 and 30 are simultaneously movable with the grinding wheels 20 and 26 by conventional apparatus (not shown). Also, the dressing wheels 28 and 30 can be rotated in the same direction as the grinding wheels 20 and 26, but at a selected different rate, or the dressing wheels 28 and 30 can be rotated in the opposite direction from the grinding wheels 20 and 26 at a selected rate. As will be understood, the grinding wheels 20 and 26 are rotated at a rate which is optimum for grinding the metal instrument being formed at the feed rate and rotation rate of the wire stock. In a like manner, the dressing wheels 28 and 30 are rotated at a rate, in a direction and either periodically or continuously in contact with the grinding wheels 20 and 30 which are optimum for dressing the grinding wheels.

As will be described in greater detail hereinbelow and as illustrated in FIG. 2, the wire stock 12 is shown just after depth calibration grooves 70, 72, 74, 76 and 78 have been ground on the wire stock 12 by the depth calibration groove grinding ribs 52, 54, 56, 58 and 60, respectively, of the second grinding wheel 26. Simultaneously with the grinding of the depth calibration grooves 70, 72, 74, 76 and 78, a tapered tip 80 is ground on the leading end of the rotating wire stock 12 by the tapered tip grinding contour 48 of the first grinding wheel 20. Also simultaneously, the previously formed tapered multi-fluted endodontic instrument 38 having a tapered tip and depth calibration grooves thereon is parted off the rotating wire stock 12 by the tapered contour 50 of the first grinding wheel 20. As mentioned above, the first and second grinding wheels 20 and 26 are illustrated in FIG. 2 after the grinding of the depth calibration grooves 70, 72, 74, 76 and 78, after the grinding of the tapered tip 80 and after the parting off of the instrument 38 and the grinding of the spiraled flutes is ready to commence. The ground metal portion of the wire stock 12 between the tapered tip 80 and the parted instrument 38 is discarded.

Referring now to FIG. 2A, the instrument 38 produced by the apparatus 10 is shown in its entirety. The instrument 38 includes a shank 90 to which a handle may be attached and which includes the depth calibration grooves 70, 72, 74, 76 and 78. Connected to the shank 90 is a tapered working portion 92 which includes three spiraled flutes 94, 95 and 96 defining a plurality of cutting edges 98. The working portion 92 of the instrument 38 terminates in the tapered tip 80.

As mentioned above, the wire stock 12 is simultaneously rotated and fed on an axis which is preferably parallel to the axes about which the first grinding wheel 20 and second grinding wheel 26 are rotated. The feed distance in which the wire stock 12 is fed per revolution of the wire stock 12 is referred to herein as the lead distance. The flute grinding ribs 40, 42 and 44 and the rolled deformed metal grinding rib 46 of the first grinding wheel 20 are separated from one another by a distance equal to the lead distance of the rotating wire stock 12 during 120° of revolution. The proper taper is formed on the working portion 92 of each produced instrument 38 by translating either the rotating wire stock 12 or the first grinding wheel 20 by conventional apparatus (not shown) so as to continuously increase the distance therebetween as the wire stock 12 is simultaneously rotated and fed during the grinding of the spiraled flutes 94, 95 and 96. As indicated above, the number of flute grinding ribs on the first grinding wheel determines the number of spiraled flutes on the instrument. The rate at which either the first grinding wheel 20 or the rotating wire stock 12 is translated determines the taper of the instrument working portion.

In the operation of the process and apparatus of this invention (referring again to FIG. 2), the first and second grinding wheels 20 and 26 are rotated about a first axis (the axes of the shafts 22 and 25), and at the beginning of each endodontic instrument producing cycle, the grinding wheels 20 and 26 are in a retracted position whereby both are out of grinding contact with the rotating wire stock 12. The rotating wire stock 12 is fed forward a predetermined distance, i.e., a distance to move the previously formed depth calibration grooves past the first grinding wheel 20 and to position the tapered grinding contour 50 thereof adjacent the point on the rotating wire stock 12 where the previously formed instrument 38 is to be parted from the rotating wire stock 12. The feed of the rotating wire stock 12 is temporarily terminated while continuing its rotation, and the first and second grinding wheels 20 and 26 are advanced into grinding contact with the rotating wire stock 12 whereby the previously formed endodontic instrument 38 is parted from the rotating wire stock 12, the tapered tip 80 is ground on the wire stock 12 by the tapered tip forming contour 48 of the first grinding wheel 20 and the depth calibration grooves 70, 72, 74, 76 and 78 are ground on the rotating wire stock 12 by the depth calibration groove grinding ribs 52, 54, 56, 58 and 60 of the second grinding wheel 26. After the previously formed instrument 38 has thus been parted from the wire stock 12 and the tapered tip and depth calibration grooves have been formed thereon, the first and second grinding wheels 20 and 26 are retracted whereby the first grinding wheel 20 is in a flute grinding position and the second grinding wheel 26 is in a position out of grinding contact with the wire stock 12 as shown in FIG. 2. Thereafter, the rotating wire stock 12 is fed past the flute grinding ribs 40, 42 and 44 and the rolled deformed metal grinding rib 46 on the first grinding wheel 20 at a controlled rate so that separate flutes 94, 95 and 96 are ground on the wire stock by the flute grinding ribs 40, 42 and 44, respectively, and rolled deformed metal is removed from the wire stock 12 by the rolled deformed metal grinding rib 46. Simultaneously with the grinding of the flutes and removal of rolled deformed metal therefrom, the first grinding wheel 20 (and the second grinding wheel 26) or the wire stock 12 are translated such that a distance between the axis of the grinding wheels 20 and 26 and the axis of the rotating wire stock increases as the wire stock is fed so as to cause the working length of the instrument being produced to be tapered. After the flutes have been ground, the first and second grinding wheels 20 and 26 are again retracted to a position out of grinding contact with the rotating wire stock 12 and the additional steps in the cycle described above are repeated.

During all or a part of each instrument producing cycle, the first and second dressing wheels 28 and 30 are in contact with the first and second grinding wheels 20 and 26, respectively, so as to maintain the required shapes, heights and distances of the grinding ribs and contours on the grinding wheels. While, as mentioned, the first grinding wheel 20 can include more or less flute grinding ribs than the three such ribs illustrated in the drawings and described herein, the most commonly produced endodontic instruments have either three flutes or four flutes. Examples of endodontic instuments with either three or four flutes are K-type files and reamers.

Referring now to FIGS. 3–8, the operation of the flute grinding ribs 40, 42 and 44 and the rolled deformed metal grinding rib 46 on the first grinding wheel 20 to form the flutes on the rotating wire stock 12 and remove rolled deformed metal (often referred to in the art as burrs) from the flutes of each endodontic instrument produced is illustrated. FIG. 3 is a cross-sectional view of the wire stock 12 prior to flutes being ground thereon. FIG. 4 illustrates the cross-section of the wire stock after the flute grinding rib 40 of the grinding wheel 20 has made grinding contact with the wire stock 12 and has formed a portion of the first flute 94. As shown in FIG. 4, the grinding of the first flute 94 causes rolled deformed metal 100 to extend from an edge of the flute in the direction that the grinding wheel 20 is rotating. When the wire stock 12 has rotated 120° and the second flute grinding rib 42 makes contact with the working portion of the wire stock 12 as shown in FIG. 5, the grinding of the second flute on the wire stock 12 is started (also shown in FIG. 5). The grinding of the second flute 95 removes the previously formed rolled deformed metal 100 from the first flute 94 by grinding it off, but additional rolled deformed metal 102 is formed along the opposite edge of the second flute 95 extending in the direction of rotation of the grinding wheel 20. After the wire stock 12 has rotated another 120° as shown in FIG. 6, the flute grinding rib 44 forms the third flute 96 whereby the rolled deformed metal 102 is removed from the second flute 95, but additional rolled deformed metal 104 is formed on the opposite edge of the third flute 96. After an additional rotation of 120° as shown in FIG. 7, the rolled deformed metal grinding rib 46 follows the identical path of the first flute grinding rib 40 whereby the rolled deformed metal 104 is ground by the rib 46 and removed from the working portion 12. Upon the completion of the flute grinding process, the fluted working portion of the wire stock 12 has a substantially burr-free cross-section as shown in FIG. 8 whereby the cutting edges 98 are sharp.

Referring now to FIGS. 9–11, a preferred form of the second dressing wheel 30 is illustrated which includes a groove depth adjustment assembly 110 for adjusting the heights of the depth calibration groove grinding ribs 52, 54, 56, 58 and 60 on the second grinding wheel 26. The adjustment assembly 110 is cylindrical in overall shape and fits within a cylindrical opening 12 in the dressing wheel 30 as best illustrated in FIGS. 9 and 10. The assembly 110 includes an insert 111 which has an arcuate diamond abrasive coated top surface 113. The insert 111 is positioned whereby it forms the bottom surface of the spaced grooves 114 formed in the diamond abrasive coated periphery of the dressing wheel 30.

The insert 111 is sealingly attached to a pedestal 116 which is adjustable in height by a pair of vertical set screws 118 and is locked in place by a pair of horizontal set screws 120. That is, as best shown in FIG. 11, the opening 112 in the grinding wheel 130 includes an enlarged upper bore 122 which intersects a smaller counterbore 124. The smaller counterbore 124 forms an annular shoulder 126 within the opening 112. The set screws 118 of the assembly 110 are threadedly connected to the pedestal 116 and rest on the annular shoulder 126. As mentioned, the set screws 118 are used to adjust the height of the surface 113 of the insert 111 with respect to the grooves 114. As will now be understood, by adjusting the height of the surface 113, the heights of the depth calibration groove grinding ribs 52, 54, 56, 58 and 60 formed on the second grinding wheel 26 by the second dressing wheel 30 are correspondingly adjusted. In order to lock the assembly 110 in the dressing wheel 30, the set screws 120 are tightened against the pedestal 116.

The dressing wheel 30 can include more than one cylindrical opening 112 and assembly 110 positioned around the periphery thereof. Preferably, two or more of the assemblies 110 are utilized. As will also now be understood, as the dressing wheel 30 is rotated against the peripheral surface of the grinding wheel 26, the arcuate surface 113 of the insert 111 contacts and adjusts the heights of the depth calibration groove grinding ribs on the grinding wheel 26.

Thus, the grinding apparatus 10 functions to mass produce endodontic instruments with a predetermined taper having a plurality of flutes, each with a predetermined number of spirals over a predetermined length of the instrument and substantially free of rolled deformed metal. The apparatus basically comprises a first grinding wheel rotated about a first axis having a plurality of flute grinding ribs and a rolled deformed metal grinding rib extending from a periphery thereof; means for feeding a rotating wire stock past the plurality of flute grinding ribs and the rolled deformed metal grinding rib at a controlled rate and on an axis so that a separate spiraled flute is ground on the wire stock by each of the flute grinding ribs and rolled deformed metal extending from the last ground flute is removed therefrom by the rolled deformed metal grinding rib; and means for translating the first grinding wheel or the wire stock such that a distance between the first and second axes increases as the wire stock is fed and a tapered multi-fluted endodontic instrument is produced.

The apparatus preferably also includes a first grinding surface on the first grinding wheel for forming a desired tip form, e.g., a tapered tip, on the rotating wire stock and a second grinding surface thereon for parting a previously formed tapered multi-fluted endodontic instrument from the rotating wire stock; a second grinding wheel rotated about a third axis having a plurality of depth indicating calibration grinding ribs extending from a periphery thereof for grinding depth indicating calibration grooves on the rotating wire stock; and means for selectively advancing and retracting the first and second grinding wheels into and out of grinding contact with the rotating wire stock.

The apparatus also preferably includes means for selectively accelerating the feed rate of the wire stock while grinding the flutes thereon and a coiled wire stock feeder which rotates on the same axis and at the same rate as the portion of the wire stock being ground.

The apparatus of this invention preferably also includes a first rotating dressing wheel in periodic or continuous contact with the first grinding wheel for dressing the peripheral surface of the first grinding wheel including the heights of the flute grinding ribs and the rolled deformed metal grinding rib thereon; and a second rotating dressing wheel in periodic or constant contact with the second grinding wheel for dressing the peripheral surface of the second grinding wheel including the heights of the depth calibration groove grinding ribs thereon.

The improved process of the present invention for producing endodontic instruments, each including a predetermined taper and a plurality of flutes having predetermined numbers of spirals over a predetermined length of the instrument, basically comprises the following steps. A first grinding wheel is rotated about a first axis having a plurality of flute grinding ribs and a rolled deformed metal grinding rib extending from a periphery thereof. A rotating wire stock is fed past the plurality of flute grinding ribs and the rolled deformed metal grinding rib at a controlled rate along a second axis so that a separate flute is ground on the wire stock by each of the flute grinding ribs and rolled deformed metal is removed from the wire stock by the rolled deformed metal grinding rib. While grinding the above mentioned flutes and rolled deformed metal, the first grinding wheel or the wire stock is translated, i.e., moved, such that a distance between the axis of the grinding wheel and the axis of the rotating wire stock increases as the wire stock is fed whereby a single pass of the rotating wire stock past the flute grinding ribs and the rolled deformed metal grinding rib produces a tapered multi-fluted endodontic instrument which is substantially free of rolled deformed metal.

The improved process of this invention preferably also includes the following steps. A first grinding surface is provided on the first grinding wheel for forming a tip of desired form on the rotating wire stock and a second surface is provided on the first grinding wheel for parting a previously formed tapered multi-fluted endodontic instrument from the rotating wire stock. A second grinding wheel is provided having a plurality of depth indicating calibration groove grinding ribs extending from a periphery thereof which is rotated about a third axis. The second grinding wheel is out of grinding contact with the rotating wire stock when the first grinding wheel is in the flute grinding position.

The first grinding wheel is retracted from a flute grinding position with the rotating wire stock to a non-grinding position, and the rotating wire stock is fed forward a predetermined distance. The feed of the rotating wire stock is temporarily terminated and the first and second grinding wheels are advanced into grinding contact with the wire stock whereby the previously formed tapered multi-fluted endodontic instrument is parted from the wire stock, a tip of desired form is ground on the wire stock and depth calibration indicating grooves are ground on the wire stock. The first and second grinding wheels are next retracted whereby the first grinding wheel is returned to the flute grinding position and the second grinding wheel is returned to a position out of contact with the wire stock. Thereafter, the feed of the rotating wire stock is resumed and the instrument forming cycle is repeated.

The improved process preferably also includes the step of selectively accelerating the feed rate of the rotating wire stock during the grinding of flutes on the wire stock, and the wire stock is preferably fed from a coiled wire feeder which rotates on the same axis and at the same rate as the portion of the wire stock being ground.

The improved process also preferably includes the steps of providing a first rotated dressing wheel for dressing the peripheral surface of the first grinding wheel including the heights of the flute grinding ribs and the rolled deformed metal grinding rib thereon, and periodically or continuously maintaining the first dressing wheel in dressing contact with the first grinding wheel.

The improved process preferably also includes the steps of providing a second rotated dressing wheel for dressing the peripheral surface of the second grinding wheel including the heights of the depth calibration groove grinding ribs thereon, and periodically or continuously maintaining the second dressing wheel in dressing contact with the second grinding wheel.

As will be understood by those skilled in the art, the endodontic instruments produced using the improved process and apparatus of this invention can be formed of any suitable metal such as stainless steel or nickel-titanium alloys. Further, as previously mentioned, the number of flutes ground on the endodontic instruments can be varied by varying the number of flute grinding ribs on the first grinding wheel, and the number and spacing of the depth calibration grooves on the instrument can be varied by varying the number and spacing of the depth calibration groove grinding ribs on the second grinding wheel.

While rolled deformed metal is substantially removed from the flutes of instruments produced by the improved process and apparatus of this invention, the produced instruments are preferably subjected to another metal burr removal step such as by contacting the instruments with air driven plastic beads or the like or by other similar techniques.

Thus, the present invention is well adapted to carry out the objects and attain the ends and advantages mentioned as well as those which are inherent therein. While numerous changes may be made by those skilled in the art, such changes are encompassed within the spirit of this invention as defined by the appended claims.

What is claimed is:

1. In a process of producing an endodontic instrument with a predetermined taper having a plurality of flutes each with a predetermined number of spirals over a predetermined length of the instrument wherein a first grinding wheel having a plurality of flute grinding ribs extending from a periphery thereof is rotated about a first axis, a rotating wire stock is fed past the plurality of flute grinding ribs at a controlled feed rate along a second axis so that a separate spiraled flute is ground on the wire stock by each of the flute grinding ribs and the grinding wheel or the wire stock is simultaneously translated such that a distance between the first and second axes increases as the wire stock is fed whereby a single pass of the wire stock past the plurality of flute grinding ribs produces a tapered multi-fluted endodontic instrument, the improvement which comprises:

providing a rolled deformed metal grinding rib on said first grinding wheel positioned to make grinding contact with said wire stock after each of said flute grinding ribs have made grinding contact with said wire stock and to follow the spiraled path of the first flute grinding rib to make grinding contact with said wire stock whereby rolled deformed metal extending from the flute last ground on said wire stock is removed therefrom.

2. The process of claim 1 wherein each of said plurality of flute grinding ribs and said rolled deformed metal grinding rib has a different height corresponding to a degree of taper of said endodontic instrument.

3. The process of claim 1 wherein said wire stock is fed such that said second axis is parallel to said first axis.

4. The process of claim 1 wherein said first grinding wheel has three flute grinding ribs extending therefrom whereby a tapered three-fluted endodontic instrument is formed by said process.

5. The process of claim 1 wherein said first grinding wheel has four flute grinding ribs extending therefrom whereby a tapered four-fluted endodontic instrument is formed by said process.

6. The process of claim 1 which further comprises the steps of:

providing a first grinding surface on said first grinding wheel for forming a tip of desired form on said rotating wire stock and a second grinding surface on said first grinding wheel for parting a previously formed multi-fluted tapered endodontic instrument from said rotating wire stock;

providing a second grinding wheel having a plurality of depth indicating calibration groove grinding ribs extending from a periphery thereof which is rotated about a third axis;

retracting said first grinding wheel from a flute grinding position with said rotating wire stock to a non-grinding position;

feeding said rotating wire stock forward a predetermined distance;

temporarily terminating the feed of said rotating wire stock;

advancing said first and second grinding wheels into grinding contact with said wire stock whereby said previously formed tapered multi-fluted endodontic instrument is parted from said wire stock, a tip of desired form is ground on said wire stock and a plurality of depth indicating calibration grooves are ground on said wire stock;

retracting said first and second grinding wheels whereby said first grinding wheel is returned to said flute grinding position and said second grinding wheel is returned to a position out of contact with said wire stock; and resuming the feed of said rotating wire stock.

7. The process of claim 1 wherein said feed rate of said rotating wire stock is selectively accelerated during the grinding of said flutes on said wire stock.

8. The process of claim 1 wherein said wire stock is fed from a coiled wire feeder which rotates on the same axis and at the same rate as the portion of said wire stock being ground.

9. An improved process for producing an endodontic instrument with a predetermined taper having a plurality of flutes each with a predetermined number of spirals over a predetermined length of the instrument comprising the steps of:

(a) providing a first grinding wheel rotated about a first axis having a plurality of flute grinding ribs and a rolled deformed metal grinding rib extending from a periphery thereof;

(b) feeding a rotating wire stock past the plurality of flute grinding ribs and the rolled deformed metal grinding rib at a controlled rate along a second axis parallel with said first axis so that a separate flute is ground on the wire stock by each of the flute grinding ribs and rolled deformed metal is removed from the wire stock by the rolled deformed metal grinding rib; and (c) simultaneously with step (b), translating said first grinding wheel or said wire stock such that a distance between said first and second axes increases as said wire stock is fed whereby a single pass of said wire stock past said flute grinding ribs and said rolled deformed metal grinding rib produces a tapered multi-fluted endodontic instrument which is substantially free of rolled deformed metal.

10. The process of claim 9 wherein each of said plurality of flute grinding ribs and said rolled deformed metal grinding rib has a different height corresponding to a degree of taper of said endodontic instrument.

11. The process of claim 9 wherein said first grinding wheel has three flute grinding ribs extending therefrom whereby a tapered three-fluted endodontic instrument is formed by said process.

12. The process of claim 9 wherein said first grinding wheel has four flute grinding ribs extending therefrom whereby a tapered four-fluted endodontic instrument is formed by said process.

13. The process of claim 9 which further comprises the steps of:

providing a first grinding surface on said first grinding wheel for forming a tip of desired form on said rotating wire stock and a second grinding surface on said first grinding wheel for parting a previously formed multi-fluted tapered endodontic instrument from said rotating wire stock;

providing a second grinding wheel having a plurality of depth indicating calibration groove grinding ribs extending from a periphery thereof which is rotated about a third axis;

retracting said first grinding wheel from a flute grinding position with said rotating wire stock to a non-grinding position;

feeding said rotating wire stock forward a predetermined distance;

temporarily terminating the feed of said rotating wire stock;

advancing said first and second grinding wheels into grinding contact with said rotating wire stock whereby said previously formed tapered multi-fluted endodontic instrument is parted from said rotating wire stock, a tip of desired form is ground on said rotating wire stock and a plurality of depth indicating calibration grooves are ground on said wire stock;

retracting said first and second grinding wheels whereby said first grinding wheel is returned to said flute grinding position and said second grinding wheel is returned to a position out of contact with said rotating wire stock; and resuming the feed of said rotating wire stock.

14. The process of claim 9 wherein said first and third axes are coincidental.

15. The process of claim 9 wherein said feed rate of said rotating wire stock is selectively accelerated during the grinding of said flutes on said wire stock.

16. The process of claim 9 wherein said wire stock is fed from a coiled wire stock feeder which rotates on the same axis and at the same rate as the portion of said rotating wire stock being ground.

17. The process of claim 10 which further comprises the steps of:
providing a first rotated dressing wheel for dressing the peripheral surface of said first grinding wheel including the heights of said flute grinding ribs and said rolled deformed metal grinding rib thereon; and
maintaining said first dressing wheel in periodic or constant dressing contact with said first grinding wheel.

18. The process of claim 17 which further comprises the steps of:
providing a second rotated dressing wheel for dressing the peripheral surface of said second grinding wheel including the heights of said depth calibration grinding ribs thereon; and
maintaining said second dressing wheel in periodic or constant dressing contact with said second grinding wheel.

19. A grinding apparatus for producing an endodontic instrument with a predetermined taper having a plurality of flutes each with a predetermined number of spirals over a predetermined length of the instrument comprising:
a first grinding wheel rotated about a first axis having a plurality of flute grinding ribs and a rolled deformed metal grinding rib extending from a periphery thereof;
means for feeding a rotating wire stock past said plurality of flute grinding ribs and said rolled deformed metal grinding rib at a controlled rate and on an axis so that a separate spiraled flute is ground on said rotating wire stock by each of said flute grinding ribs and rolled deformed metal extending from the last ground flute is removed therefrom by said rolled deformed metal grinding rib; and
means for translating said first grinding wheel or said rotating wire stock such that a distance between said first and second axes increases as said wire stock is fed and a tapered multi-fluted endodontic instrument is produced.

20. The apparatus of claim 19 wherein each of said plurality of flute grinding ribs and said rolled deformed metal grinding rib has a different height corresponding to a degree of taper of said endodontic instrument.

21. The apparatus of claim 19 wherein said rotating wire stock is fed such that said second axis is parallel to said first axis.

22. The apparatus of claim 19 wherein said first grinding wheel has three flute grinding ribs extending therefrom whereby a tapered three-fluted endodontic instrument is formed by said process.

23. The apparatus of claim 19 wherein said first grinding wheel has four flute grinding ribs extending therefrom whereby a tapered four-fluted endodontic instrument is formed by said process.

24. The apparatus of claim 19 which further comprises:
said first grinding wheel including a first grinding surface thereon for forming a tip of desired form on said rotating wire stock and a second grinding surface thereon for parting a previously formed tapered multi-fluted endodontic instrument from said rotating wire stock;
a second grinding wheel rotated about a third axis having a plurality of depth indicating calibration groove grinding ribs extending from a periphery thereof for grinding depth indicating calibration on said rotating wire stock; and
means for selectively advancing and retracting said first and second grinding wheel into and out of grinding contact with said rotating wire stock.

25. The apparatus of claim 19 which further comprises means for selectively accelerating the feed rate of said wire stock.

26. The apparatus of claim 19 which further comprises a coil feeder which rotates on the same axis and at the same rate as the portion of the wire stock being ground.

27. The apparatus of claim 19 wherein said first and third axes are coincidental.

28. The apparatus of claim 19 which further comprises a first rotated dressing wheel in periodic or constant contact with said first grinding wheel for dressing the peripheral surface of said first grinding wheel including the heights of said flute grinding ribs and said rolled deformed metal grinding rib thereon.

29. The apparatus of claim 19 which further comprises a second rotated dressing wheel in periodic or constant contact with said second grinding wheel for dressing the peripheral surface of said second grinding wheel including the heights of said depth calibration grinding ribs thereon.

* * * * *